US008134014B2

(12) United States Patent
Richter et al.

(10) Patent No.: US 8,134,014 B2
(45) Date of Patent: Mar. 13, 2012

(54) PREPARATION OF URETDIONE POLYISOCYANATES

(75) Inventors: Frank Richter, Leverkusen (DE); Andreas Hecking, Langenfeld (DE); Reinhard Halpaap, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/315,286

(22) Filed: Dec. 2, 2008

(65) Prior Publication Data

US 2009/0143558 A1 Jun. 4, 2009

(30) Foreign Application Priority Data

Dec. 4, 2007 (DE) .......................... 10 2007 058 487

(51) Int. Cl.
 *C07D 205/00* (2006.01)
 *C08G 18/81* (2006.01)
(52) U.S. Cl. .................. 548/952; 548/335.1; 548/951; 540/200; 540/201; 540/202; 560/334; 252/182.2; 528/45; 528/48; 528/49; 528/52
(58) Field of Classification Search ............ 548/951, 548/952; 560/334, 330, 336; 540/200, 201, 540/202; 528/45, 48, 49, 52; 252/182.2
See application file for complete search history.

(56) References Cited

U.S. PATENT DOCUMENTS

| 4,476,054 A | 10/1984 | Disteldorf et al. |
| 4,912,210 A * | 3/1990 | Disteldorf et al. ............ 540/202 |
| 4,929,724 A | 5/1990 | Engbert et al. |
| 5,461,020 A * | 10/1995 | Goldstein et al. ............. 502/167 |
| 7,067,654 B2 | 6/2006 | Richter et al. |
| 7,151,151 B2 | 12/2006 | Richter et al. |
| 2004/0049028 A1 | 3/2004 | Laas et al. |
| 2004/0059082 A1 | 3/2004 | Laas et al. |
| 2004/0106789 A1 | 6/2004 | Richter et al. |
| 2005/0113551 A1 | 5/2005 | Richter et al. |
| 2008/0176747 A1* | 7/2008 | Zipse et al. ................... 504/235 |

FOREIGN PATENT DOCUMENTS

| DE | 10244216 A1 * | 4/2004 |
| GB | 821158 | 9/1959 |
| GB | 1145952 A | 3/1969 |
| GB | 1153815 A | 5/1969 |

OTHER PUBLICATIONS

Zipse, Hendrik, Xu, Shangjie, Held Ingmar, Modular Desing of Pyridine-Based Acyl-Transfer Catalysts, Feb. 2, 2007, Synthesis 2007, No. 8, pp. 1185-1196.*
Hans Josef Laas et al, "Zur Synthese aliphatischer Polyisocyanate-Lackpolyisocyanate mit Biuret-, Isocyanurat-oder Uretdionstruktur", J. prakt. Chem., (month unavailable) 1994, p. 185-200, 336.
Ingmar Held et al, "Modular Design of Pyridine-Based Acyl-Transfer Catalysts", Synthesis, (month unavailable) 2007, p. 1185-1196, No. 8.

* cited by examiner

*Primary Examiner* — Milton I Cano
*Assistant Examiner* — Michael L Leonard
(74) *Attorney, Agent, or Firm* — Robert S. Klemz; Noland J. Cheung

(57) ABSTRACT

The invention relates to the use of specific pyridines as catalysts for the dimerization of isocyanates (uretdione formation) and a process for preparing polyisocyanates having a high content of uretdione groups.

3 Claims, No Drawings

PREPARATION OF URETDIONE POLYISOCYANATES

CROSS-REFERENCE TO RELATED APPLICATIONS

The present application claims the right of priority under 35 U.S.C. §119(a)-(d) of German Patent Application Number 10 2007 058 487.5, filed Dec. 4, 2007.

BACKGROUND OF THE INVENTION

The invention relates to the use of specific pyridine derivatives as catalysts for the dimerization of isocyanates (uretdione formation) and a process for preparing polyisocyanates having a high content of uretdione groups.

Aliphatic polyisocyanates which contain uretdione groups and are based on optionally branched, linear-aliphatic diisocyanates have a particularly low viscosity. Products based on aromatic, araliphatic or cycloaliphatic diisocyanates are generally highly viscous to solid substances which can be used, inter alia, as elimination-free, internally blocked crosslinkers in coating systems.

An overview of isocyanate oligomerization is given in J. Prakt. Chem./Chem. Ztg. 1994, 336, 185-200.

Tris(dialkylamino)phosphines (DE-A 3 030 513), if appropriate in combination with cocatalysts (DE-A 3 437 635), display a good selectivity for the formation of uretdione groups (uretdione selectivity).

DE-A 1 670 720 discloses the preparation of aliphatic polyisocyanates containing uretdione groups, in which tertiary phosphines having at least one aliphatic substituent and also boron trifluoride and its adducts are used as catalysts. It is indicated that high proportions of uretdione groups in the product can be obtained only at low conversions and reaction temperatures in the range from 50 to 80° C., with isocyanate trimers (isocyanurates and iminooxadiazinediones) and, especially at relatively high temperature, other by-products such as carbodiimides or uretonimines being formed at the same time. Uretonimines are particularly undesirable since they tend to liberate monomeric diisocyanate during storage.

DE A 10254878 describes the use of phosphines having at least one cycloaliphatic, P-bonded radical as catalysts for NCO dimerization. These catalysts display a significantly higher uretdione selectivity than other trialkylphosphines. The use of a specific case of these phosphines, viz. representatives bearing bicyclic radicals, for the same use is described in DE 10354544.

However, all phosphines suffer from the common disadvantage of air sensitivity, which makes their industrial use more difficult. Their uretdione selectivity is also strongly dependent on the reaction temperature and the degree of conversion of the monomer.

DE A 3 739 549 discloses catalytic NCO dimerization using 4-dialkylaminopyridines such as 4-dimethylaminopyridine (DMAP), but uretdione formation proceeds selectively only in the case of specific cycloaliphatic isocyanates such as isophorone diisocyanate (IPDI). Linear-aliphatic isocyanates such as hexamethylene diisocyanate (HDI) and also branched, linear-aliphatic isocyanates such as trimethylhexane diisocyanate (TMDI) and methylpentane diisocyanate (MPDI) give mainly strongly colored, heterogeneous reaction products when using DMAP and related compounds.

It is surprising that pyridine derivatives which are substituted by N atoms in the 3 and 4 positions on the pyridine ring, with the latter two N atoms being bridged by means of a two-membered, saturated ($sp^3$-hybridized) carbon segment, are extremely effective catalysts for uretdione formation not only in the case of IPDI but also convert linear-aliphatic isocyanates such as hexamethylene diisocyanate (HDI) into virtually trimer-free polyisocyanates.

SUMMARY OF THE INVENTION

The present invention is related to a process for the dimerization of isocyanates, comprising reacting
  a) at least one organic isocyanate,
  b) a catalyst containing at least one pyridine derivative corresponding to the basic structure of the formula (I)

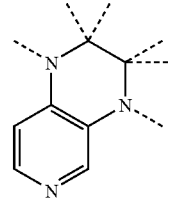

formula (I)

c) optionally solvents and
  d) optionally additives.

DETAILED DESCRIPTION OF THE PREFERRED EMBODIMENTS

For the purposes of the present invention, the term "trimer" is the sum of the isomeric structures formed from isocyanates by "trimerization", viz. isocyanurates and iminooxadiazinediones.

The invention also provides for the use of pyridine derivatives corresponding to the basic structure of the formula (I)

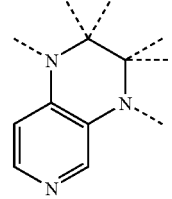

formula (I)

in the dimerization of isocyanates (uretdione formation).

The carbon atoms of the ethylene bridge connecting the two nitrogen atoms are $sp^3$-hybridized and thus have two substituents in each case. The two ethylenically bridged N atoms each have a substituent which is preferably not hydrogen.

Preferred pyridines for uretdione formation from isocyanates correspond to the formula (II)

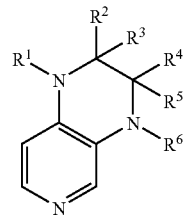

formula (II)

where
  $R^1$, $R^6$ are, independently of one another, identical or different, substituted or unsubstituted and/or branched hydrocarbon radicals, R², R⁴ are, independently of one another, hydrogen or identical or different hydrocarbon radicals which may be substituted by heteroatoms or functional groups and/or be branched and R³, R⁵ are, independently of one another, radicals having the definition of the radicals R², R⁴ or together form a cyclic, 4- to 7-membered hydrocarbon segment which bridges the two N atoms and may be substituted by hydrocarbon radicals, heteroatoms or functional groups and/or be unsaturated.

The stereochemical arrangement of the radicals R² to R⁵ relative to one another in formula (II) have been chosen purely arbitrarily.

If R², R⁴ are hydrocarbon radicals, they can be either linear-aliphatic or else cycloaliphatic or aromatic. If R², R⁴ are linear-aliphatic, they preferably have from 1 to 12, particularly preferably from 1 to 6, carbon atoms. If R², R⁴ are cycloaliphatic, they preferably have from 3 to 12, particularly preferably from 3 to 6, carbon atoms. If R², R⁴ are aromatic, they preferably have from 6 to 20, particularly preferably from 6 to 12, carbon atoms.

R², R⁴ can be substituted by heteroatoms or ether groups.

R³, R⁵ either correspond to the above definition of the radicals R², R⁴ including the preferred ranges or together form a bridging radical of the abovementioned type which preferably has from 4 to 20, particularly preferably from 4 to 12, carbon atoms and may be substituted by heteroatoms or functional groups and/or be unsaturated.

Preferred compounds of the formula (II) are those in which R¹ and R⁶ are, independently of one another, identical or different alkyl groups which are preferably selected from the group consisting of methyl, ethyl, propyl and butyl, R² and R⁴ are, independently of one another, H or identical or different alkyl groups selected from the group consisting of methyl, ethyl, propyl and butyl and R³ and R⁵ together form a 1,3-propylene, 1,3-butylene, 2,4-pentylene, 1,4-butylene, 1,4-pentylene, 2,4-hexylene, 1,2-cyclopentylene or 1,2-cyclohexylene bridge.

For the present purposes, "propyl" and "butyl" in each case encompass all corresponding isomeric compounds.

Examples of 3,4-diaminopyridines which can be used according to the invention are those of the formulae (III) to (XI) below:

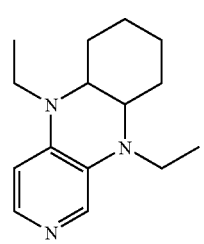

III

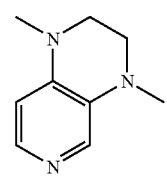

IV

-continued

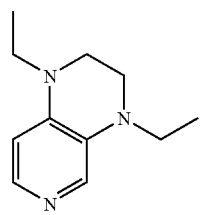

V

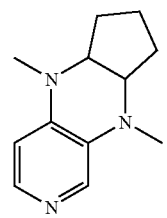

VI

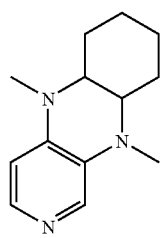

VII

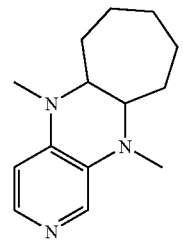

VIII

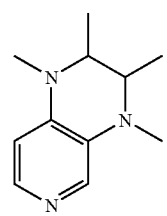

IX

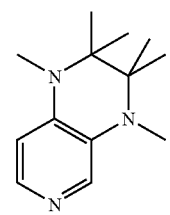

X

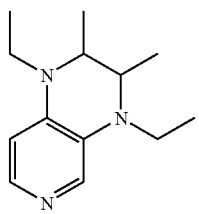

XI

These can be used as catalyst for uretdione formation either individually, in any mixtures with one another or in mixtures with other catalysts of the prior art.

The amount of catalyst to be used in the process of the invention depends first and foremost on the isocyanate used and the desired reaction rate and is in the range from 0.01 to 5 mol %, based on the sum of the molar amounts of the isocyanate used and the catalyst. Preference is given to using from 0.05 to 2 mol % of catalyst.

The catalyst b) can be used undiluted or as a solution in solvents in the process of the invention. Possible solvents include many compounds, for example: halogenated or unhalogenated, aliphatic or aromatic hydrocarbons, alcohols, ketones, esters and ethers.

As isocyanates to be used according to the invention in a), it is in principle possible to use all known organic isocyanates prepared by phosgenation or by phosgene-free processes, either individually or in any mixtures with one another.

Preference is given to using aliphatic, cycloaliphatic, aromatic or araliphatic diisocyanates or polyisocyanates having an NCO functionality of $\geq 2$.

Examples which may be mentioned are tolylene diisocyanate (TDI), bis(isocyanatophenyl)methane and polyphenylpolymethylene polyisocyanates prepared by condensation of aniline and formaldehyde and subsequent phosgenation (MDI), hexamethylene diisocyanate (HDI), isophorone diisocyanate (IPDI) and bis(isocyanatocyclohexyl)methane.

The process of the invention is carried out so that the conversion of the NCO groups is preferably from 5 to 90 mol %, in particular from 10 to 60 mol %, very particularly preferably from 10 to 50 mol %.

The process of the invention is usually carried out in the temperature range from 0° C. to 150° C.

To achieve conversions of the NCO groups in the above ranges, the reaction is stopped at the desired degree of conversion.

To stop the reaction after reaching the desired degree of conversion, it is possible to use a number of previously described catalyst poisons (DE A 1670666, 1670720, 3437635), in particular alkylating agents, e.g. dimethyl sulphate, methyl toluenesulphonate, or acylating agents, e.g. acid chlorides or acid anhydrides, which are reacted with the catalyst, if appropriate with an increase in temperature (variant A).

After deactivation of the reaction mixture according to variant A, unreacted monomer and/or the deactivated catalyst can be separated off.

The process can also be stopped without chemical deactivation of the catalyst. For this purpose, the active catalyst is separated off from the reaction mixture immediately after the desired conversion has been reached in order to prevent further reaction, possibly with by-product formation (variant B).

Unreacted monomer can be separated off from the reaction mixture treating according to variant B simultaneously with or after removal of the catalyst.

In the process of the invention, the removal of unreacted monomers, the catalyst and/or other undesirable constituents from the reaction mixture can be carried out using all known separation techniques such as distillation, extraction or crystallization/filtration. Preference is given to distillation, if appropriate in the specific embodiment of thin film distillation. Of course, combinations of two or more of these techniques can also be employed.

To stop the reaction according to variant B, the catalyst is preferably removed by distillation, possibly with unreacted monomer being removed at the same time.

In the work-up of a reaction mixture stopped according to variant A or B, the residual monomer present is preferably removed by distillation.

If the polyisocyanate prepared according to the invention is still to contain free, unreacted monomer, as is of interest, for example, for further processing to produce NCO-blocked products or low-NCO or NCO-free polyuretdione hardeners, e.g. for powder coatings, the removal of monomer after termination of the reaction (variants A and B) can be omitted.

In carrying out the process of the invention, it is immaterial whether the process is carried out entirely or partly batchwise or continuously.

Furthermore, additives and stabilizers customary in polyisocyanate chemistry can be added at any point in time in the process of the invention. Examples are antioxidants such as sterically hindered phenols (2,6-di-tert-butylphenol, 4-methyl-2,6-di-tert-butylphenol), light stabilizers such as HALSs, triazoles, etc., weak acids or catalysts for the NCO—OH reaction, e.g. dibutyltin dilaurate (DBTL).

Furthermore, it can be useful to add small amounts of a catalyst poison as used in variant A to a product worked up according to variant B in order to increase the redissociation stability and to suppress by-product formation, discolouration or further reaction of the free NCO groups with one another, e.g. during storage of the product.

Products which have been prepared by the process of the invention and are based on branched or unbranched, linear-aliphatic diisocyanates or polyisocyanates which do not have any cycloalkyl substituents have a viscosity of <1000 mPas/23° C. If cycloaliphatic, aromatic and/or araliphatic diisocyanates or polyisocyanates are used, highly viscous to solid resins are obtained (viscosity>10 000 mPas/23° C.).

In low-monomer form, i.e. after unreacted monomer has been separated off, the products according to the invention have an NCO content of <30% by weight, preferably<25% by weight.

The polyisocyanates prepared by the process of the invention serve as starting materials for producing, for example, shaped bodies (which may be foamed), paints and varnishes, coating compositions, adhesives or aggregates, with the free NCO groups which have not been converted into uretdione which are present being able to be blocked if appropriate.

The free NCO groups which have not been converted into uretdione can be blocked by means of all methods known to those skilled in the art. As blocking agents, it is possible to use, in particular, phenols (e.g. phenol, nonylphenol, cresol), oximes (e.g. butanone oxime, cyclohexanone oxime), lactams (e.g. ε-caprolactam), secondary amines (e.g. diisopropylamine), pyrazoles (e.g. dimethylpyrazole), imidazoles, triazoles or malonic and acetic esters.

The largely by-product-free polyisocyanates containing uretdione groups which have been prepared by the process of the invention can be used, in particular, for producing one- and two-component polyurethane coatings, if appropriate in admixture with other diisocyanates or polyisocyanates of the prior art, e.g. diisocyanates or polyisocyanates containing biuret, urethane, allophanate, isocyanurate and iminooxadiazinedione groups.

Particular preference is likewise given to using the polyisocyanates based on branched or unbranched linear-aliphatic isocyanates which have been prepared according to the invention as reactive diluents for reducing the viscosity of relatively highly viscous polyisocyanate resins.

To convert the polyisocyanates prepared according to the invention into a polyurethane, it is possible to use all compounds having at least two isocyanate-reactive functions, either individually or in any mixtures with one another (isocyanate-reactive binder).

Preference is given to using one or more isocyanate-reactive binders which are known per se in polyurethane chemistry, e.g. polyhydroxy compounds or polyamines. As polyhydroxy compounds, particular preference is given to using polyester polyols, polyether polyols, polyacrylate polyols and/or polycarbonate polyols, if appropriate with addition of low molecular weight, polyhydric alcohols.

The equivalence ratio between isocyanate groups which have not been converted into uretdione and may, if appropriate, also be blocked and isocyanate-reactive functions of the isocyanate-reactive binder, e.g. OH, NH or COOH, is from 0.8 to 3, preferably from 0.8 to 2.

It is possible to use an excess of isocyanate-reactive binder, since the cleavage of the uretdione ring, if appropriate at elevated temperature and/or with addition of catalyst, leads to liberation of further NCO groups which can react with the excess of isocyanate-reactive functions. This results in an increase in the network density of the polymer formed and has an advantageous effect on its properties.

To accelerate the crosslinking reaction of the polyisocyanates prepared according to the invention with the isocyanate-reactive binder, it is possible to use all catalysts known from polyurethane chemistry. For example, it is possible to use metal salts such as dibutyltin(IV)dilaurate, tin(II)bis(2-ethylhexanoate), bismuth(II)tris(2-ethylhexanoate), zinc(II)bis(2-ethylhexanoate) or zinc chloride and also tertiary amines such as 1,4-diazabicyclo[2.2.2]octane, triethylamine or benzyldimethylamine.

In making up the formulation, the blocked or unblocked polyisocyanate prepared according to the invention, the isocyanate-reactive binder, catalyst(s) and if appropriate the customary additives such as pigments, fillers, other additives, levelling agents, antifoams and/or matting agents are mixed and homogenized in a customary mixing apparatus such as a sand mill, if appropriate using solvents.

Suitable solvents are all customary surface coating solvents known per se, e.g. ethyl or butyl acetate, ethylene or propylene glycol monomethyl, monoethyl or monopropyl ether acetate, 2-butanone, 4-methyl-2-pentanone, cyclohexanone, toluene, xylene, solvent naphtha, N-methylpyrrolidone, etc.

The coating compositions can be applied in solution or from the melt or, if appropriate, in solid form (powder coatings) to the article to be coated by customary methods such as painting, rolling, casting, spraying, dipping, fluidized-bed sintering or electrostatic spray processes.

Suitable substrates are all known materials, in particular metals, wood, plastics and ceramic.

EXAMPLES

The NCO content of the resins described in the examples and comparative examples was determined by titration in accordance with DIN 53 185.

The dynamic viscosities were determined at 23° C. using a VT 550 viscometer from Haake, Karlsruhe. It was ensured by means of measurements at different shear rates that the flow behaviour of the respective polyisocyanates prepared according to the invention and also that of the comparative products corresponds to that of ideal newtonian fluids. Indication of the shear rate can therefore be omitted.

The figures for "mol %" or "molar ratio of various structural types" are based on NMR-spectroscopic measurements. They are always based, unless indicated otherwise, on the sum of the structural types formed by the modification reaction (oligomerization) from the previously free NCO groups of the isocyanates to be modified.

$^{13}$C-NMR measurements were carried out on DPX 400, AVC 400 or DRX 700 instruments from Bruker, Karlsruhe, Del., using approximately 50% strength samples in dry CDCl$_3$ or using approximately 80% strength samples in D$_6$-DMSO ($^{13}$C-NMR: 100 or 176 MHz, relaxation delay: 4 sec, min. 2000 scans). As reference for the ppm scale, small amounts of tetramethylsilane in the appropriate solvent ($\delta$=0 ppm) or the solvent alone ($\delta$=77.0 ppm (CDCl$_3$) or $\delta$=43.5 ppm (D$_6$-DMSO)) were chosen.

Unless indicated otherwise, the reactions were carried out using freshly degassed HDI or IPDI as starting material. The expression "freshly degassed" means that the diisocyanate used was freed of dissolved gases by stirring for at least 30 minutes under reduced pressure (<1 mbar) and subsequently placed under nitrogen immediately before the catalytic reaction.

All reactions were carried out under an atmosphere of dry nitrogen.

The catalysts used were prepared by methods known from the literature (Synthesis 2007, No. 8, 1185-1196). In the examples according to the invention, the catalysts (III) and (IV) as per the above formulae in the description were used.

Examples 1 and 2 According to the Invention, and also 3 and 4, Comparative Examples 10 g of freshly degassed HDI (Examples 1 and 3) or IPDI (Examples 2 and 4) were in each case stirred at 23° C. under nitrogen in the presence of 2 mol % of catalyst (III) (Examples 1 and 2) or N,N,-dimethylaminopyridine (DMAP) (Examples 3 and 4) by means of a magnetic stirrer bar in glass vessels closed by means of a septum, with the progress of the reaction being checked at regular intervals by measurement of the index of refraction (at 20° C. and the frequency of the light of the D line of the sodium spectrum: $n_D^{20}$) of the reaction mixture (cf. Table 1). After 135 minutes, the reaction mixture was analysed by means of NMR spectroscopy. After 24 hours, the reaction mixtures from Examples 1 and 2 were highly viscous and could no longer be stirred by means of a magnetic stirrer bar, while those from Examples 3 and 4 were still readily stirrable. The behaviour of the mixtures from Examples 3 and 4 demonstrates the significantly higher activity of the catalyst according to the invention compared that of the prior art (DMAP).

|  | Example 1 according to the invention | Example 2 according to the invention | Example 3 comparison | Example 4 comparison |
|---|---|---|---|---|
| Catalyst | (III) | (III) | DMAP | DMAP |
| Isocyanate | HDI | IPDI | HDI | IPDI |
| $n_D^{20}$ at t$_0$* | 1.4581 | 1.4846 | 1.4580 | 1.4859 |
| t = 15 min | 1.4595 | 1.4851 | 1.4593 | 1.4862 |
| Colour: | pale yellow | colourless | deep red-orange | pale yellow |

-continued

|  | Example 1 according to the invention | Example 2 according to the invention | Example 3 comparison | Example 4 comparison |
|---|---|---|---|---|
| t = 75 min | 1.4653 | 1.4897 | 1.4605 | 1.4866 |
| t = 135 min | 1.4711 | 1.4968 | 1.4701 | 1.4906 |
| Molar ratio of uretdione: "trimers" | 97:3 | no isocyanurate detectable | 2:1 | 98:2 |

*Beginning of reaction; catalyst completely dissolved

Example 5, According to the Invention

Catalyst: (III) (0.24 mol %, based on HDI); reaction temperature: 40° C.

400 ml of HDI were placed in a double-walled flange vessel which was maintained at 40° C. by means of an external circuit and was provided with stirrer, reflux condenser, connected to an inert gas unit (nitrogen/vacuum) and thermometer and degassed. After admission of nitrogen, 1.5 g of catalyst In were added and the mixture was stirred at 40° C. for the time indicated in Table 2. The index of refraction of the mixture ($n_D^{20}$) rose to 1.4760. The reaction mixture was subsequently worked up without prior deactivation of the catalyst. The work-up was carried out by vacuum distillation in a thin film evaporator of the sort-path evaporator (SPE) type provided with upstream prevaporiser (PV) (distillation data: pressure: 0.08 mbar, PV temperature: 140° C., MV temp.: 150° C., distillation time: 1 h), with unreacted monomer being separated off together with the active catalyst as distillate and the polyisocyanate resin containing uretdione groups being obtained as bottom product (start of run: Example 5-0).

The distillate containing the active catalyst was collected in a second stirred flange apparatus which had an identical construction to the first and was made up with fresh degassed HDI to the initial amount (400 ml) immediately after the end of the distillation. The mixture was subsequently stirred again at 40° C. for the time indicated in Table 2 and worked up by distillation as described above (Example 5-A). This procedure was repeated a total of three times (to Experiment 5-C).

When the experiment was repeated in an analogous way but using DMAP in place of (D), the first distillation run did not give a usable polyisocyanate resin but only poor yields of a highly viscous, strongly discoloured, inhomogeneous material which is suitable neither as polyisocyanate per se nor for further processing, e.g. in powder coating crosslinkers. The distillate obtained is virtually inactive.

TABLE 2

Catalyst: (III) (0.24 mol %, based on HDI); reaction temperature: 40° C., semicontinuous reaction procedure

| Ex. 5 | Reaction time [hh:mm] | Yield of resin [g] | NCO content [%] | Viscosity [mPas] at 23° C. |
|---|---|---|---|---|
| 0 | 24:00 | 198 | 19.7 | 100 |
| A | 22:55 | 161 | 20.7 | 70 |
| B | 23:15 | 124 | 21.3 | 60 |
| C | 25:50 | 99 | 21.7 | 50 |

Example 6, According to the Invention

Catalyst: (IV) (0.2 mol %, based on HDI); reaction temperature: 40° C.

The procedure of Example 5 was repeated except that 450 ml of HDI and 0.9 g of catalyst of the formula IV were used.

TABLE 3

Catalyst: (IV) (0.2 mol %, based on HDI); reaction temperature: 40° C., semicontinuous reaction procedure

| Ex. 6 | Reaction time [hh:mm] | Yield of resin [g] | NCO content [%] | Viscosity [mPas] at 23° C. |
|---|---|---|---|---|
| 0 | 24:00 | 140 | 21.7 | 60 |
| A | 22:00 | 80 | 23.0 | 50 |
| B | 23:30 | 40 | 23.2 | 53 |
| C | 25:50 | 28 | 23.3 | 50 |

The structural composition of the resins from Examples 5 and 6 is identical. The resins are virtually pure HDI uretdiones, >95 mol % of uretdione structures, also isocyanurate and iminooxadiazinedione structures, the latter <5% in total.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the dimerization of isocyanates comprising reacting:
    a) at least one organic isocyanate,
    b) a catalyst containing at least one pyridine derivative corresponding to the formula (II)

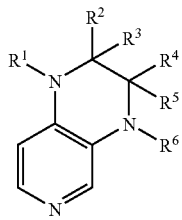

formula (II)

where
  $R^1$, $R^6$ are, independently of one another, identical or different, substituted or unsubstituted and/or branched hydrocarbon radicals,
  $R^2$, $R^4$ are, independently of one another, hydrogen or identical or different hydrocarbon radicals which may be substituted by heteroatoms or functional groups and/or be branched and
  $R^3$, $R^5$ are, independently of one another, radicals having the definition of the radicals $R^2$, $R^4$ or together form a cyclic, 4- to 7-membered hydrocarbon segment which bridges the two N atoms and may be substituted by hydrocarbon radicals, heteroatoms or functional groups and/or be unsaturated c) optionally solvents and
d) optionally additives are reacted.

2. Process according to claim 1, characterized in that, in formula (II)

R$^1$ and R$^6$ are, independently of one another, identical or different alkyl groups selected from the group consisting of methyl, ethyl, propyl and butyl, R$^2$ and R$^4$ are, independently of one another, H or identical or different alkyl groups selected from the group consisting of methyl, ethyl, propyl and butyl and R$^3$ and R$^5$ together form a 1,3-propylene, 1,3-butylene, 2,4-pentylene, 1,4-butylene, 1,4-pentylene, 2,4-hexylene, 1,2-cyclopentylene or 1,2-cyclohexylene bridge.

3. Process according to claim 1, wherein the pyridines used correspond to one of the formulae (III) to (XI)

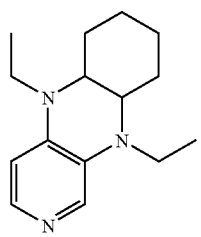

III

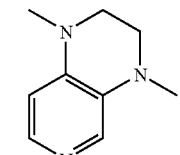

IV

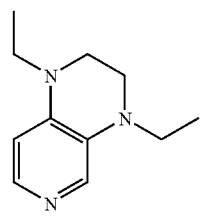

V

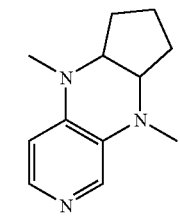

VI

-continued

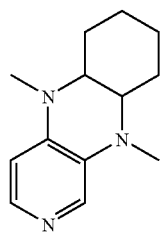

VII

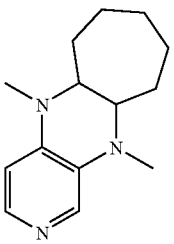

VIII

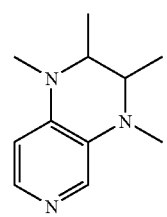

IX

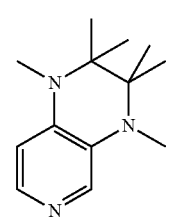

X

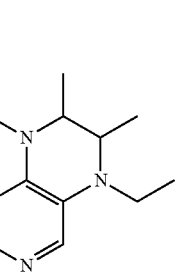

XI

* * * * *